(12) United States Patent
Herve (10) Patent No.: US 8,440,839 B2
(45) Date of Patent: May 14, 2013

(54) DINITROPYRAZOLE DERIVATIVES, THEIR PREPARATION, AND ENERGETIC COMPOSITIONS COMPRISING THEM

(75) Inventor: Gregoire Herve, Verberie (FR)

(73) Assignees: Herakles, La Haillan (FR); Eurenco, Paris (FR)

( * ) Notice: Subject to any disclaimer, the term of this patent is extended or adjusted under 35 U.S.C. 154(b) by 0 days.

(21) Appl. No.: 13/595,622

(22) Filed: Aug. 27, 2012

(65) Prior Publication Data

US 2012/0323017 A1    Dec. 20, 2012

Related U.S. Application Data

(60) Division of application No. 12/314,726, filed on Dec. 16, 2008, now Pat. No. 8,273,784, which is a continuation-in-part of application No. PCT/IB2008/002535, filed on Jun. 6, 2008.

(30) Foreign Application Priority Data

Jun. 12, 2007 (FR) .................................. 07 55679
Jun. 6, 2008 (FR) .................................. 08 53768

(51) Int. Cl.
*A61K 31/415* (2006.01)
*C07D 231/38* (2006.01)

(52) U.S. Cl.
USPC .............. 548/366.1; 548/372.1; 548/366.4; 548/366.7; 548/367.4; 514/407

(58) Field of Classification Search ............ 514/407; 548/366.1, 366.4, 366.7, 367.4, 372.1
See application file for complete search history.

(56) References Cited

PUBLICATIONS

C. Sharts, "N,N-Difluoroalkylamines by Direct Fluorination of Alkylamines[1]", *The Journal of Organic Chemistry* vol. 33, No. 3, Mar. 1968, pp. 1008-1011.

R. Schmidt et al., "Synthesis of 4-Amino-3,5-dinitro-1*H*-pyrazole Using Vicarious Nucelophilic Substitution of Hydrogen", *J. Heterocyclic Chem.*, 38, (2001), pp. 1227-1230.

V.P. Lebedev et al., "Thermochemical and explosive properties of nitropyrazoles", International Annual Conference of ICT, vol. 29, Jan. 1, 1998, pp. 180-1-180-13.

J. Janssen et al., "Phyrazoles. XII. The Preparation of 3(5)-Nitropyrazoles by Thermal Rearrangement of N-Nitropyrazoles[1,2]", *The Journal of Organic Chemistry*, vol. 38, No. 10, May 18, 1973, pp. 1777-1782.

I.L. Dalinger et al., "Synthesis of 4-diazo-3,5-dinitropyrazole and characteristic features of its behaviour towards nucleophiles", *Mendeleev Commun.* 1997, pp. 58-59.

C. Habraken et al., "Nucleophilic Substitution Reactions on *N*-Nitropyrazoles[1]", *J. Org. Chem.*, vol. 42, No. 17, 1977, pp. 2893-2895.

Dalinger, "N-(Difluoroamino)azoles—a new class of N-substituted azoles", Mendeleev Communications, 1996, (1), pp. 13-15.

Ugrak, "Nitrogen-15 and oxygen-17 NMR spectral parameters of N-nitropyrazoles", Mendeleev Communications, 1993, (3), pp. 109-110.

*Primary Examiner* — Sreeni Padmanabhan
*Assistant Examiner* — Sahar Javanmard
(74) *Attorney, Agent, or Firm* — Clark & Brody (57) ABSTRACT

The present invention provides:
dinitropyrazole derivatives of formula (I)

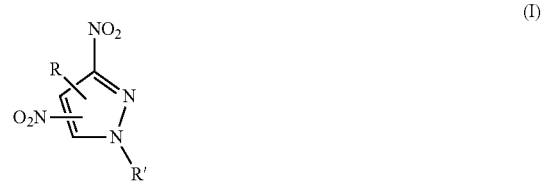

(I)

in which: R=$NO_2$, $NH_2$, $NF_2$, NHOH, OH or $NHNH_2$ and R'=H when R=$NH_2$, $NF_2$, NHOH, OH or $NHNH_2$ or R'=H, $NH_2$ or a linear or branched $C_1$-$C_4$ alkyl group, optionally substituted by at least one hydroxy and/or one fluoro group, when R=$NO_2$; other than 4-amino-3,5-dinitropyrazole; and also the salts of said derivatives of formula (I) in which R'=H;

the preparation of said derivatives and of their salts; and
energetic compositions comprising at least one of said derivatives and/or at least one salt of such a derivative.

5 Claims, 1 Drawing Sheet

DINITROPYRAZOLE DERIVATIVES, THEIR PREPARATION, AND ENERGETIC COMPOSITIONS COMPRISING THEM

This application is a Divisional of U.S. Ser. No. 12/314,726 filed on Dec. 16, 2008, which is a Continuation-in-Part of PCT/IB2008/002535 filed on Jun. 6, 2008, which is published as WO2008/152525 on Dec. 18, 2008.

FIELD OF THE INVENTION

The present invention relates to:
new heterocyclic molecules: new derivatives of dinitropyrazoles (of 3,5-dinitropyrazole and of 3(5),4-dinitropyrazole);
the preparation of said new molecules;
energetic compositions comprising such molecules; and
synthesis intermediates, which are new products, useful in the preparation of said new molecules.
These new compounds (these new molecules) are of particular advantage in that they exhibit both a high energetic performance and a reduced vulnerability.

BACKGROUND ART

Reduced vulnerability munitions (known as MURAT for MUnition with Risk ATtenuation), developed a decade and a half ago, necessitate the use of explosive molecules of little or no sensitivity. These molecules are required to possess a sensitivity which is as low as possible, while retaining a heightened level of energetic performance. But these two properties are difficult to reconcile. For instance, cyclotetramethylene tetranitramine (octogen) is the most widespread explosive to date, but has a level of insensitivity (essentially to impact) which is inadequate for application to MURAT-type munitions. 3-Nitro-1,2,4-triazol-5-one (ONTA), for its part, is an energetic molecule which is entirely exceptional in terms of insensitivity, being markedly less sensitive than octogen, for example. On the other hand, its level of energetic performance is lower than that of octogen. The same is true of other low-sensitivity explosive molecules, such as 1,3,5-triamino-3,4,6-trinitrobenzene (TATB), 1,1'-diamino-2,2'-dinitroethylene (FOX-7) or 4,6-di-(3-amino-5-nitro-1,2,4-triazole)-5-nitropyrimidine (FR 2,624,118).

The skilled worker is constantly looking for new energetic molecules which offer an advantageous tradeoff in terms of performance and vulnerability while retaining a level of thermal stability that meets the demands of the application. Such molecules advantageously exhibit characteristics of thermodynamic decomposition that allow them to be used in the fields of propulsion and of explosives.

Lebedev et al. showed calculated and/or measured results of physico-chemical properties and of performances for energetic compounds (INTERNATIONAL ANNUAL CONFERENCE OF ICT, vol. 29, 1 janvier 1998, p. 180.1-180.13). The developed chemical formulae of said compounds together with said results are shown in Tables. It has to be emphasized that the synthesis (that any process for the preparation) of the concerned compounds, more particularly the one of compounds of formula VII, VIII, IX, are neither disclosed, nor suggested. To the inventor's knowledge, no additional information has since been published related to these compounds and their process of preparation, except information on 4-amino-3,5-dinitro-1-pyrazole (compound of formula IX) (see the following paragraph). The inventor notably discloses a non obvious process for the preparation of the 5-amino-3,4-dinitro-1-pyrazole further in the present text (within the scope of the present invention).

R. D. Schmidt, G. S. Lee, P. F. Pagoria, A. R. Mitchell and R. Gilardi, in J. Heterocyclic Chem. 2001, 38, 1227, described the synthesis and properties of a new explosive: 4-amino-3,5-dinitro-1-pyrazole (LLM-116). This new explosive is presented as being advantageous in reference to the tradeoff referred to above: sensitivity/performance. Nevertheless, it has the major disadvantage of dissolving small polar organic molecules such as DMSO and of undergoing hydration in the presence of water. However, the product is advantageous, in performance terms, only if it is free from any trace of impurity, and the purification and dehydration process is long and laborious.

The skilled worker is therefore still looking for new energetic molecules which comply with the specification set out above and which, furthermore, advantageously, can be synthesized readily.

SUMMARY OF THE INVENTION

The present invention provides, in accordance with its first subject, a new class of energetic molecules. These energetic molecules are new dinitropyrazole derivatives, new derivatives of 3,5-dinitropyrazole and of 3(5),4-dinitropyrazole. Said derivatives conform to the formula (I) below:

in which: R=$NO_2$, $NH_2$, $NF_2$, NHOH, OH or $NHNH_2$;
R'=H when R=$NH_2$, $NF_2$, NHOH, OH or $NHNH_2$, or
R'=H, $NH_2$ or a linear or branched $C_1$-$C_4$ alkyl group, optionally substituted by at least one hydroxy and/or one fluoro group,
when R=$NO_2$.

It is appropriate to exclude 4-amino-3,5-dinitropyrazole from said new class, since it has already been described (see above).

The compounds of the invention—new derivatives of dinitropyrazoles—accordingly consist of:
the compounds of formula (I) above in which R'=H; in other words, the compounds conforming to the following formula:

in which: R=$NO_2$, $NH_2$, $NF_2$, NHOH, OH or $NHNH_2$ (with the exception of 4-amino-3,5-dinitropyrazole); and
the N-substituted 3,4,5-trinitropyrazoles identified above, conforming to the formula (Ic) below.

The new derivatives of the invention, in the neutral acid form (R'=H), are capable of existing in the form of salts, of formula (I'):

in which $C^+$ represents a cation.

Said salts form an integral part of the first subject of the present invention.

The skilled worker has already understood that the compounds of the invention of formula (I) in which R'=H (in neutral acid form or in salt form) exist as two families, that of the derivatives of 3,5-dinitropyrazole (of formulae Ia and I'a below) and that of the derivatives of 3(5),4-dinitropyrazole (of formulae Ib and I'b below); with 3,4,5-trinitropyrazole and its salts being common to both said families:

(Ia)

(I'a)

in which: R=NO$_2$, NF$_2$, NHOH, OH or NHNH$_2$;

(Ib)

(I'b)

in which: R=NO$_2$, NH$_2$, NF$_2$, NHOH, OH or NHNH$_2$.

The invention further provides compounds of formula (I) in which R' is other than H, more specifically 3,4,5-trinitropyrazole derivatives which conform to the formula (Ic) below:

(Ic)

in which R'=NH$_2$ or a linear or branched C$_1$-C$_4$ alkyl group which is optionally substituted by at least one hydroxy group and/or one fluorine.

R' is an amino group or a lower alkyl group (containing 1 to 4 carbon atoms), which is optionally substituted. Said lower alkyl group may be linear or branched. It is selected from methyl, ethyl, n-propyl, isopropyl, n-butyl, isobutyl and tert-butyl groups and is unsubstituted or substituted by at least one hydroxy group and/or at least one fluorine. More particularly it may consist of a perfluorinated lower alkyl group. According to one advantageous variant, R' is an amino group (—NH$_2$) or a methyl group (—CH$_3$). Very advantageously it is a methyl group.

These compounds of the invention, of formula (I) in which R=NO$_2$ and R' is other than H, have a melting point which is lower than that of the compounds of the invention of formula (I) in which R'=H. Their energetic power, which is reduced to a greater or lesser extent, remains of interest owing to the presence of the three nitro groups. Said compounds may in any case be doped by their joint use with at least one other, more highly performing energetic molecule, of the type for example of RDX (cyclotrimethylene trinitramine or hexogen), HMX (cyclotetramethylene tetranitramine or octogen), CL20 (2,4,6,8,10,12-hexanitrohexaazaisowurtzitane or HNIW), or another nitrogen-containing heterocycle known to date (see later on below).

The low melting point of said compounds is of particular interest. It allows each of the said compounds to be formulated as a melt-cast explosive by a method (of explosives manufacture) that is familiar to the skilled worker. Said method does not involve a binder and does not include powder tableting. It consists primarily in melting the energetic compound or compounds in question by a simple raising of the temperature, and then in causing the melted mass to crystallize by simple cooling. Advantageously the melted mass is filled with at least one other, more highly performing, energetic molecule (more particularly, of the types identified above).

N-Methyl-3,4,5-trinitropyrazole is thus a particularly interesting compound of the invention in that it combines a low melting point (91.3° C.) with interesting energetic properties (more particularly it exhibits an oxygen balance significantly greater than that of TNT).

In the context of its first subject, therefore, the present invention encompasses the new compounds of formula (I) identified below:
4-hydroxy-3,5-dinitropyrazole,
4-hydroxylamino-3,5-dinitropyrazole,
4-hydrazino-3,5-dinitropyrazole,
4-difluoramino-3,5-dinitropyrazole,
5-hydroxy-3,4-dinitropyrazole,
5-amino-3,4-dinitropyrazole,
5-hydroxylamino-3,4-dinitropyrazole,
5-hydrazino-3,4-dinitropyrazole,
5-difluoramino-3,4-dinitropyrazole,
3,4,5-trinitropyrazole,
the salts of said compounds,
N-methyl-3,4,5-trinitropyrazole, and
N-amino-3,4,5-trinitropyrazole.

Particular preference is given to the compounds of formula (I) below:
3,4,5-trinitropyrazole,
4-hydroxy-3,5-dinitropyrazole,
4-hydroxylamino-3,5-dinitropyrazole,
5-hydroxy-3,4-dinitropyrazole,
5-amino-3,4-dinitropyrazole,
5-hydroxylamino-3,4-dinitropyrazole,
their salts,
N-methyl-3,4,5-trinitropyrazole, and
N-amino-3,4,5-trinitropyrazole.

With regard to the salts of the compounds of the invention (those of formula (I) in which R'=H), it may be said, without any limitation, that they conform advantageously to the formulae (I'), (I'a) or (I'b) above in which C⁺ represents:

an alkali metal cation (such as $Li^+$, $Ca^+$, $K^+$, $Cs^+$), an alkaline earth metal cation (such as $Mg^{2+}$, $Ba^{2+}$), an ammonium cation, a substituted ammonium cation (substituted more particularly by a hydroxyl group (hydroxylammonium), by lower alkyl groups ($C_1$-$C_6$, advantageously $C_1$-$C_4$, alkyl) and/or aryl groups, which are themselves optionally substituted; the presence of such substituents allows the energetic power of the compounds to be modified), a hydrazinium cation, a guanidinium cation, an aminoguanidinium cation, a diaminoguanidinium cation, an iminium cation.

The compounds of the invention are energetic compounds of low sensitivity, or even no sensitivity, which are highly performing. Their level of energetic performance is equivalent, or in some cases even superior, to that of octogen, for levels of sensitivity which are comparable with those of ONTA. Said compounds of the invention are therefore particularly advantageous:

in that they are both highly energetic and of reduced vulnerability;

in that they comply, in a particularly advantageous way, with the specification below:

energetic performance levels higher than those of ONTA or than those of TATB;

very low sensitivity;

high thermal stability (required for the intended applications).

The statements above are demonstrated in the example section further on in the present text.

According to a second subject, the present invention provides the preparation of the new compounds of the formula (I) and their salts.

The majority of compounds of formula (I) can be obtained from "new precursors" which belong to the family of the trinitropyrazoles (1,3,4 and 3,4,5 isomers), which are themselves obtained from known dinitropyrazoles. The compounds of formula (I) (in which R'=H) in question are obtained by substitution on trinitropyrazole heterocycles.

The known dinitropyrazoles conform to the formulae specified below and accordingly have been described in the literature. The formulae and corresponding bibliographic references are indicated below.

described in J. Heterocyclic Chem. 2001, 38, 1227 (see above);

described in J. Org. Chem. 1973, 38, 1777 (by J. W. A. M. Janssen, H. J. Koeners, C. G. Kruse, C. L. Habraken).

The trinitropyrazoles—"new precursors"—conform to the formulae below:

The first of them—3,4,5-trinitropyrazole—is a compound of the invention (of formula (I) in which R=$NO_2$ and R'=H), which can be used as a precursor for the preparation of other compounds of the invention:

those of formula (Ia) in which R=NH—$NH_2$, OH and NHOH (see below); and those of formula (Ic) in which (R=$NO_2$ and) R' is other than H.

The second of them—1,3,4-trinitropyrazole—is a new intermediate which is useful in the preparation of compounds of the invention (of formula (Ib) in which R=NH—$NH_2$, OH, NHOH, $NH_2$ and $NF_2$).

Described below in greater detail is the second subject of the present invention, namely the process for preparing the compounds of formula (I) and their salts.

Said process comprises:

A) for preparing 4-difluoroamino-3,5-dinitropyrazole:
  fluorinating 4-amino-3,5-dinitropyrazole;

B) for preparing other compounds of formula (I) in which R'=H:
  obtaining an isomer of trinitropyrazole selected from 3,4,5-trinitropyrazole and the 1,3,4-trinitropyrazole intermediate, respectively, by oxidizing 4-amino-3,5-dinitropyrazole or nitrating 3,5-dinitropyrazole and by nitrating 3,4-dinitropyrazole;
  carrying out a substitution:
  on said 1,3,4-trinitropyrazole intermediate, to give 3,4-dinitropyrazoles substituted in position 5 by the radical R=NH—$NH_2$, OH, NHOH or $NH_2$;
  on said 3,4,5-trinitropyrazole, to give 3,5-dinitropyrazoles substituted in position 4 by the radical R=NH—$NH_2$, OH or NHOH;
  fluorinating the resulting 5-amino-3,4-nitropyrazole to give 5-difluoroamino-3,4-nitropyrazole;

C) for obtaining a salt, reacting the resulting compound of formula (I) (in which R'=H) with a base; and D) for preparing a compound of formula (I) in which R'≠H:
  obtaining 3,4,5-trinitropyrazole by oxidation of 4-amino-3,5-dinitropyrazole, nitration of 3,5-dinitropyrazole, oxidation of 5-amino-3,4-dinitropyrazole or diazotization of said 5-amino-3,4-dinitropyrazole, said 5-amino-3,4-dinitropyrazole having been prepared as indicated above;
  obtaining its anion;
  carrying out a nucleophilic substitution on said anion.

The different steps of sections A and B above are given in the reaction scheme below.

Specified below are each of said steps, leading to the preparation of the trinitropyrazole intermediate (1,3,4-trinitropyrazole) and of each of the compounds of formula (I).

4-Difluoroamino-3,5-dinitropyrazole is obtained directly by fluorination of 4-amino-3,5-dinitropyrazole (known starting product). In the same way, the fluorination of 5-amino-3,4-dinitropyrazole (product of the invention prepared beforehand) leads to 5-difluoroamino-3,4-dinitropyrazole. The conventional and long-established methods of fluorination, more particularly those described in J. Org. Chem. 1968, 33, 1008-11, are ideally suitable.

3,4,5-Trinitropyrazole can also be obtained, directly, by three different synthesis routes:

by oxidation of 4-amino-3,5-dinitropyrazole (or of its isomer 5-amino-3,4-dinitropyrazole).

Indeed, it is noted that said trinitropyrazole may in the same way be obtained by oxidation of 5-amino-3,4-dinitropyrazole prepared beforehand. The oxidation reaction, in one context or the other, is advantageously carried out in concentrated peroxides. A concentrated mixture of $H_2O_2+H_2SO_4$ is suitable for the oxidation of deactivated amines. Selective extraction of the medium is necessary. It is advantageous to use dichloromethane as the extraction solvent. Examples 3 and 4 below illustrate an oxidation of this kind;

by diazotization of 5-amino-3,4-dinitropyrazole (prepared beforehand).

Operation takes place in solution in a concentrated inorganic acid, such as, for example, 20% sulfuric acid. More highly concentrated acids may be employed, without recording any notable effect on the yield. The intermediate diazonium salt is converted to trinitropyrazole by heating the acidic solution in the presence of sodium nitrite. Example 3' below illustrates a diazotation of this kind. The same diazotization reaction starting from 4-amino-3,4-dinitropyrazole appears to be more awkward to carry out, owing to the superior stability of the diazonium salt (on this point reference may be made to I. L. Dalinger, T. I. Cherkasova, S. A. Shevelev, *Mendeleev Commun.* 1997, 58).;

by nitration of 3,5-dinitropyrazole, under severe conditions.

The Applicant has indeed shown that the nitration of 3(5), 4-dinitropyrazole, under moderate temperature conditions (between 0° C. and ambient temperature), leads to the selective formation of 1,3,4-trinitropyrazole (see below), while the nitration of 3,5-dinitropyrazole, under severe conditions (more particularly as regards temperature), leads to the selective formation of 3,4,5-trinitropyrazole. The preparation of 1,3,4-trinitropyrazole (new intermediate) is specified below. With regard to the nitration of 3,5-dinitropyrazole, which leads directly to 3,4,5-trinitropyrazole, it is carried out in a sulfonitric ($H_2SO_4+HNO_3$) or phosphonitric ($H_3PO_4+HNO_3$) medium, containing from 0 to 100% by mass of sulfuric, phosphoric or nitric anhydride (referred to as oleums), at a temperature between 50° C. and the boiling temperature of the medium. This route to the 3,4,5-trinitropyrazole of the invention—an original and particularly advantageous route to a high-performance compound—is illustrated in Example 5 below.

1,3,4-Trinitropyrazole—new intermediate—is therefore obtained by nitration, under moderate temperature conditions (see above), of 3(5),4-dinitropyrazole. Such a nitration may be carried out at ambient temperature in an acetonitric ($HNO_3$+acetic anhydride) mixture or equivalent mixture, such as mixtures of $HNO_3$+trifluoroacetic anhydride. A nitration of this kind in an acetonitric mixture is illustrated in Example A below. It has been shown, moreover, in the context of the invention, that nitronium solutions are likewise suitable. The solutions of nitronium ions may be generated directly from nitronium salts (such as $NO_2BF_4$), or from nitric acid catalyzed by $H_2SO_4$. A procedure of this kind is illustrated in Example B below.

Starting from said 3,4,5-trinitropyrazole (compound of the invention, of formula (I) in which $R=NO_2$), it is possible, by nucleophilic substitution, to obtain other compounds of formula (I) (in which $R=H$) of the invention. Starting from said 1,3,4-trinitropyrazole (new intermediate) it is possible, by substitution, to obtain other compounds of formula (I) (in which $R=H$) of the invention The substitution reactions are carried out in the presence of inorganic bases such as solutions of hydroxides, ammonia, hydrazine, and hydroxylamine to form the appropriately substituted dinitropyrazoles of formula (I). The hydroxide solutions may be generated starting from hydrogen carbonate, carbonate, hydroxide (sodium or potassium hydroxide), or nitrite salts or even water. The reactions may be carried out in water or in organic solvents such as dimethylformamide, dimethyl sulfoxide, tetrahydrofuran, acetonitrile, nitromethane, sulfolane, and mixtures thereof. Said reactions may be carried out at a temperature between temperatures lower than 0° C. and the reflux temperature of the solvent used. Preferably the substitution reactions of 3,4,5-trinitropyrazole are performed at high temperatures (reflux) and the substitution reactions of 1,3,4-trinitropyrazole are performed at low temperature. In fact, as described in the article by Habraken and Poels (*J. Org. Chem.* 1977, 42, 2893), the substitution reactions on 1,4-dinitropyrazole derivatives, such as 1,3,4-trinitropyrazole, lead to the functionalization of the 5 position of the pyrazole and to substitution of the N-nitro. In contrast, under more vigorous conditions, the nucleophilic substitution on the 3,4,5-trinitropyrazole takes place, unexpectedly, on the carbon (4) of the pyrazole.

To obtain 5-amino-3,4-dinitropyrazole, the substitution reaction concerned is an amination. The techniques of amination that are known are numerous. Mention may be made, for example, of the reaction with ammonia (mentioned above), the method of Gabriel (via the phthalamide derivative), and the reduction of an azide derivative. Advantageously it is possible thus to prepare, selectively, 5-amino-3,4-dinitropyrazole, in two steps:

the reaction of azide salts with 1,3,4-trinitropyrazole to form 5-azido-3,4-dinitropyrazole, a new compound (see, for illustration, Example C below);

the reduction of said 5-azido-3,4-dinitropyrazole by conventional methods, such as the action of a trisubstituted phosphine or of thiolacetic acid (see, for illustration, Examples 1 and 2 below).

These two steps are shown schematically below:

-continued

It is recalled, incidentally, that said 5-amino-3,4-dinitropyrazole is able, by oxidation or diazotization, to give 3,4,5-trinitropyrazole (see above);
and is able, by fluorination, to give 4-difluoroamino-3,5-dinitropyrazole (see above).

To obtain a salt of any one of the compounds of formula (I) in which R'=H, said compound is reacted with the appropriate base (of formula COH, according to the formula of the salts that was given above).

For preparing an N-substituted 3,4,5-trinitropyrazole, therefore, the 3,4,5-trinitropyrazole as obtained at the outcome of any one of the four pathways shown in the reaction scheme above and described above (oxidation of 4-amino-3,5-dinitropyrazole or of 5-amino-3,4-dinitro-pyrazole, nitration of 3,5-dinitropyrazole or diazotization of 5-amino-3,5-dinitropyrazole) is used.

The reaction scheme is as follows:

In the presence of an organic or inorganic base, such as NaOH, KOH, NaH, an alkoxide or pyridine, the anion of 3,4,5-trinitropyrazole is obtained. This anion, in the presence of an appropriate electrophile, undergoes a nucleophilic substitution which gives rise to the expected compound.

The methyl compound, for instance, may be obtained by the action of a conventional methylating agent, such as methyl iodide, methyl triflate, diazomethane or trimethyloxonium salts. The other alkyl compounds may be obtained analogously.

For instance, the amino compound may be obtained by electrophilic amination, by the action of a conventional electrophilic aminating agent, such as chloramine ($NH_2Cl$), hydroxylamine-O-sulfonic acid (HOSA, $NH_2$—O—$SO_3H$), dinitrophenoxy-O-hydroxylamine, trinitrophenoxy-O-hydroxylamine (or Pic-O—$NH_2$=hydroxylamine of picric acid).

The conditions for implementation of the nucleophilic substitution are conventional per se. The original feature is the precise nature of the anion in question.

According to the third of its subjects, the present invention provides the new intermediates which are useful in preparing the compounds of formula (I) (and their salts). Said new intermediates, identified in the above description of the process, consist of:
1,3,4-trinitropyrazole; and
5-azido-3,4-dinitropyrazole.

The new compounds of formula (I) of the invention:
as identified above, in general form (formulae (I), (Ia), (Ib) and (Ic)) and specifically (see the list of said compounds set out earlier), and/or
as (readily) obtainable by the process described above (limited to a single step (for obtaining 3,4,5-trinitropyrazole and obtaining 4-difluoroamino-3,5-dinitropyrazole) or comprising, more generally, 2 or 3 steps (for obtaining other compounds of formula (I) in which R'=H) exhibit energetic characteristics which are particularly advantageous (with regard to the sensitivity/performance tradeoff and to the thermal stability). Their performance characteristics are advantageous for both propellant applications and explosive applications.

The compounds of the invention (and their salts) clearly constitute advantageous competitors to the insensitive energetic molecules represented by ONTA, TATB and I-RDX®. They are serious candidates for MURAT-type applications in explosives and in propellants of greatly reduced vulnerability relative to conventional propellants.

According to its third subject, therefore, the present invention provides energetic compositions comprising at least one compound of formula (I) (in which R'=H or R'≠H) and/or at least one salt of such a compound (of formula (I) in which R'=H), as described above.

The determination of the effective amount of said at least one compound and/or salt is within the scope of the skilled worker, in view of the exact end use desired for said energetic compositions. Said energetic compositions may more particularly consist of explosive compositions or propellant compositions. These two types of energetic compositions (with conventional energetic molecules) are familiar to the skilled worker.

The energetic compositions of the invention of the first type—explosive compositions—contain or do not contain binder (inert or energetic). They generally contain at least 20% by mass of at least one compound of formula (I) (in which R'=H or R'≠H) and/or of at least one salt of such a compound (of formula (I) in which R'=H), very generally at least 50% by mass of such a compound of formula (I) (idem) and/or at least one salt of such a compound (idem). They are entirely able to contain between 90% by mass and 100% by mass of at least one such compound of formula (I) (idem) and/or of at least one salt of such a compound (idem).

The energetic compositions of the invention of the second type—propellant compositions—contain a binder, inert or energetic. They generally contain not more than 80% by mass of at least one compound of formula (I) (in which R'=H or R'≠H) and/or of at least one salt of such a compound (of formula (I) in which R'=H), very generally not more than 50% by mass of a compound of formula (I) (idem) and/or of at least one salt of such a compound (idem).

The energetic compositions of the invention for which a specification has been given above, in no way limitatively, of the amount of compound(s) of the invention (compound(s) of formula (I) in which R'=H or R'≠H and/or salts of compounds of formula (I) in which R'=H) are compositions which are generally obtained by tableting a powder or with involvement of a binder (at a more or less considerable level).

Obviously also an integral part of the third subject of the present invention (i.e., energetic compositions comprising at least one compound or salt of the invention) are the energetic compositions of melt-cast type which comprise at least one compound of the invention which has a low melting point, in other words at least one compound of formula (I) in which R'≠H (and R=$NO_2$).

Said melt-cast energetic compositions comprise at least one such compound (generally one such compound) or at least one such compound (generally one such compound) with at least one other, known energetic molecule which is more highly performing. Said at least one other energetic molecule is advantageously selected from conventional energetic molecules such as HMX, RDX, CL20 and another nitrogen-containing heterocycle (see above).

The presence of at least one other (more highly performing) energetic molecule of this kind is not mandatory; it is advantageous. Generally, when it is present, at least one other energetic molecule of this kind is present at from 10% to 80% by mass. Its presence at a level of 60% by mass is especially recommended.

DETAILED DESCRIPTION OF THE PREFERRED EMBODIMENTS

Figure 1:
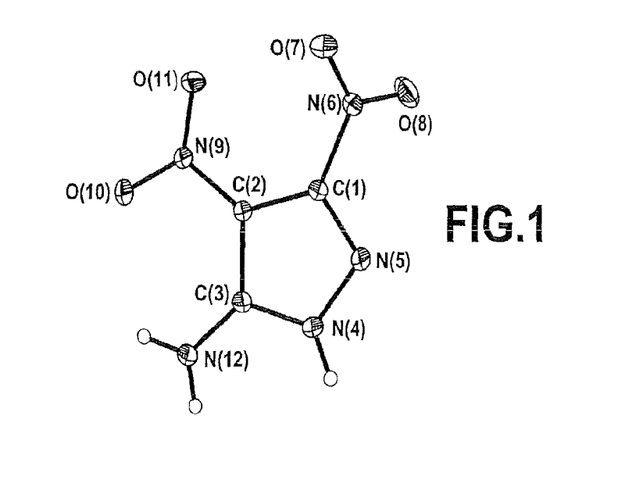
FIG. 1 shows a structure of a first product of the invention using x-ray diffraction.
Figure 2:
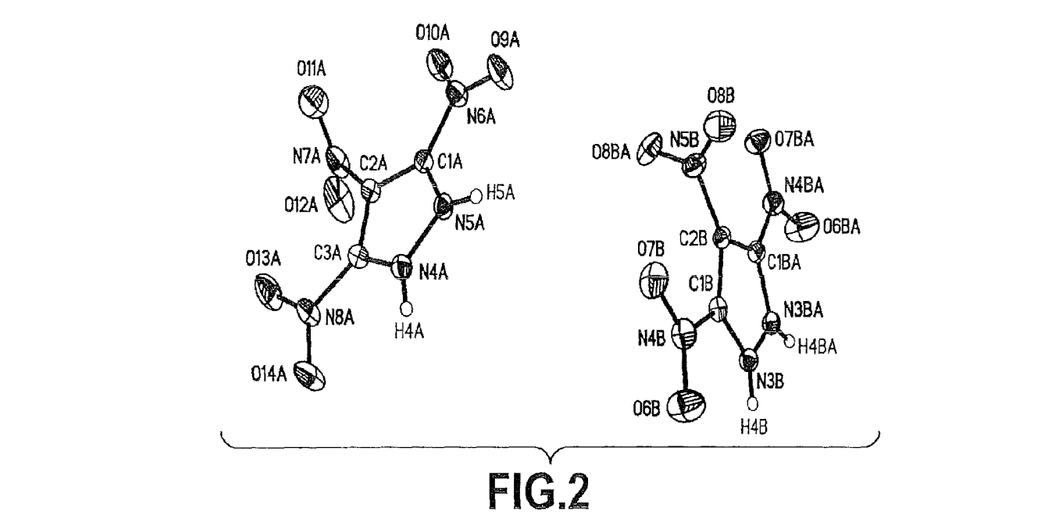
FIG. 2 shows a structure of a second product of the invention using x-ray diffraction.
Figure 3:
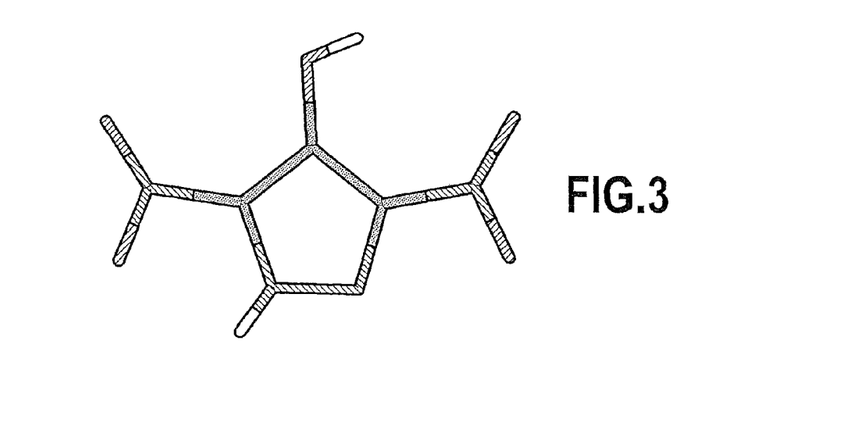
FIG. 3 shows a structure of a third product of the invention using x-ray diffraction.

The invention will now be illustrated by the examples below.
Examples A, B and C illustrate the preparation of synthesis intermediates.
Examples 1 to 6 illustrate the preparation of dinitropyrazole derivatives according to the invention: of formula (I) in which R=NH$_2$, NO$_2$, OH (see Table 1 below) and R'=H. The properties and performance characteristics of these compounds are of interest (see Tables 2 to 4 below). Attached FIGS. 1, 2, and 3 show the structures of said compounds as determined by means of X-rays.
Examples 7 and 8 illustrate the preparation of N-substituted 3,4,5-trinitropyrazoles.

Example A 200 mg of 3,4-dinitropyrazole are introduced into 7 mL of acetic anhydride containing 1.4 mL (2.13 g) of concentrated nitric acid at 0° C. The temperature is allowed to rise to 15° C., and the mixture is then stirred at this temperature for 18 hours. The reaction mixture is poured onto 70 g of ice and then the product is extracted with dichloromethane. The chlorinated organic phase is dried over magnesium sulfate and then filtered and concentrated under vacuum. 200 mg of crude product are recovered in this way. The 1,3,4-trinitropyrazole is purified on silica gel with elution with a hexane/AcOEt (2/0.5, v/v) mixture. 34 mg of pure, colorless liquid are recovered (13% yield). $^1$H NMR (acetone): 8.49 (s, CH); $^{13}$C NMR (acetone): 128.6 (CH), 128.4 (CNO$_2$, broad), 145.1 (t, CNO$_2$); $^{14}$N NMR (acetone): 310.3, 314, 351.5 ppm. DSC: decomposition temperature: 191° C.

Example B

With argon blanketing at 0° C., 200 mg of 3,4-dinitropyrazole are introduced into 20 mL of anhydrous acetonitrile containing 193 mg of nitronium tetrafluoroborate. The reaction mixture is then left to react at ambient temperature for 18 hours. It is subsequently concentrated under vacuum, then treated with 30 mL of ice-water and extracted with dichloromethane. The recovery and purification phase is identical to that described in Example A. Purification gives 121 mg of pure, colorless liquid (47% yield).

Example C

A solution of 1,3,4-trinitropyrazole, described in Examples A and B, diluted in 5 mL of tetrahydrofuran is poured slowly into a stirred suspension of sodium azide in dimethyl sulfoxide (28 mL) at ambient temperature. After 1 hour of stirring, the reaction mixture is poured onto 280 g of ice, then acidified to a pH of 1 using 37% hydrochloric acid solution. The mixture is extracted with 60 mL of diethyl ether. The organic phase is recovered and then washed with 0.1 N HCl, dried over magnesium sulfate, and concentrated under vacuum. The product is subsequently triturated in 10 mL of dichloromethane until a yellow solid is obtained. The 5-azido-3,4-dinitropyrazole is filtered and then dried under vacuum for 30 minutes. This gives 220 mg of yellow solid, which is used as it is in the subsequent phase (23% yield). $^1$H NMR (acetone): no signal. $^{13}$C NMR (acetone) (ppm): 118.1 (Q), 140.6 (Q), 150.1 (Q). $^{14}$N NMR (acetone) (ppm): 357.1 (NO$_2$), 355.4 (NO$_2$), 310.3 (N$_3$), 231. DSC: melting point: 141.3° C.; decomposition temperature: 156.7° C.

Example 1

200 mg of 5-azido-3,4-dinitropyrazole are reduced in 10 mL of thiolacetic acid at ambient temperature for 2 days. Subsequently 20 mL of hexane are poured in to precipitate the product. 50 mg of yellow solid are recovered in this way by filtration (28% yield).
The structural formula of said product and the results of physicochemical analyses ($^1$H, $^{13}$C, and $^{14}$N NMR and MS), which confirm the structure, are given in Table 1 below.

Example 2

At ambient temperature and in one portion, 287 mg of triphenylphosphine are added to 20 mL of tetrahydrofuran containing 200 mg of 5-azido-3,4-dinitropyrazole. The reaction mixture is stirred at ambient temperature for 18 hours and then 5 mL of distilled water are added. The reaction mixture is left to react at reflux for 20 hours. Subsequently 10% sodium hydroxide solution is added in order to raise the pH to 10-11. The reaction mixture is washed with ethyl acetate twice (20 mL), then acidified to an acid pH of 1 using 10% hydrochloric acid. The product is subsequently extracted with 20 mL of diethyl ether (3 times). The ethereal phases are combined and then washed with saturated sodium chloride solution, dried over sodium sulfate, and concentrated under vacuum. The product is subsequently triturated in 20 mL of dichloromethane, before being filtered and dried. This gives 65 mg of red solid (51% yield).
The structural formula of said product and the results of physicochemical analyses ($^1$H, $^{13}$C, and $^{14}$N NMR and MS), which confirm the structure, are given in Table 1 below.

Example 3

600 mg of 5-amino-3,4-dinitropyrazole are added all at once to a well-stirred mixture of sodium persulfate (3 g), 60% hydrogen peroxide (2.5 g), and concentrated sulfuric acid (4 g) at ambient temperature. The reaction mixture is stirred for 8 hours and then extracted 5 times with dichloromethane (5*20 mL). The chlorinated phases are combined and are dried over magnesium sulfate, filtered, and then concentrated under vacuum. This gives 217 mg of pure product (31% yield).

Example 3'

650 mg of sodium nitrite are added rapidly at 0-10° C. to a 20% solution of sulfuric acid (5 mL) containing 145 mg of 5-amino-3,4-dinitropyrazole. The mixture is left to react at this temperature for 1 hour and then the cold mixture is poured into 40 mL of 10% strength aqueous sodium nitrite which is maintained at 20° C. The mixture is subsequently heated at 50-60° C. for 30 minutes until the effervescence disappears completely. The excess sodium nitrite is then neutralized by addition of concentrated sulfuric acid. The reaction mixture is extracted 3 times with ethyl acetate. The organic phases are combined, washed with a brine, dried over magnesium sulfate, filtered and then concentrated. 3,4,5-Trinitropyrazole is obtained in the form of an orange gum with a crude yield of 80%. The NMR and IR analyses are in accordance with those obtained with the product of Example 3.

Example 4

600 mg of 4-amino-3,5-dinitropyrazole are added all at once to a well-stirred mixture of sodium persulfate (3 g), 60% hydrogen peroxide (2.5 g), and concentrated sulfuric acid (4 g) at ambient temperature. The reaction mixture is stirred for 8 hours and then extracted 5 times with dichloromethane (5*20 mL). The chlorinated phases are combined and are dried over magnesium sulfate, filtered, and then concentrated under vacuum. This gives 325 mg of pure product (47% yield).

The structural formula of said product and the results of physicochemical analyses ($^1$H, $^{13}$C, and $^{14}$N NMR and MS), which confirm the structure, are given in Table 1 below.

Example 5

202 mg of 3,5-dinitropyrazole are dissolved in 6 g of concentrated sulfuric acid. 4 g of fuming nitric acid are added rapidly at ambient temperature. Subsequently, using a dropping funnel, 6 g of sulfuric oleum containing 60% $SO_3$ (mass titer) are added. The temperature of the reaction mixture is allowed to rise. The mixture is subsequently heated at 70° C. for 1 hour. The reaction mixture is left to cool to ambient temperature before being hydrolyzed in 30 g of ice. The mixture is extracted 3 times with ethyl acetate. The organic phases are combined and are washed with saturated sodium chloride solution, dried over magnesium sulfate, filtered, and then concentrated under vacuum. This gives 245 mg of pure product (95% yield).

The structural formula of said product and the results of physicochemical analyses ($^1$H, $^{13}$H, and $^{14}$N NMR and MS), which confirm the structure, are given in Table 1 below.

Example 6

140 mg of 3,4,5-trinitropyrazole are added all at once to a solution of 200 mg of sodium hydroxide (10 mL). The mixture is heated at reflux for 3 hours. The mixture is subsequently acidified to a pH of 1-2 using 10% hydrochloric acid solution, then extracted with ethyl acetate 3 times. The organic phases are combined and are dried over sodium sulfate, filtered, then concentrated under vacuum. The solid residue is taken up in 10 mL of dichloromethane and then filtered. 40 mg of yellow solid are collected in this way.

The structural formula of said product and the results of physicochemical analyses ($^1$H, $^{13}$C, and $^{14}$N NMR), which confirm the structure, are given in Table 1 below.

Said Table 1 is given below.

TABLE 1

| | Example | | |
|---|---|---|---|
| | 1, 2 | 3, 3', 4, 5 | 6 |
| formula | $NH_2$ group with $O_2N$, $O_2N$ on pyrazole N—H | $NO_2$ group with $O_2N$, $O_2N$ on pyrazole N—H | $NO_2$ group with OH, $O_2N$ on pyrazole N—H |
| $^1$H NMR (ppm) | 7.31 (broad) | 12.3 (broad) | 11.4 (very broad) |
| $^{13}$C NMR (ppm) | 109.8, 148.7, 150.3 | 122.6 (t), 143.2 | 135.2, 139.9 |
| $^{14}$N NMR (ppm) | 359 | 348.9 | 310.5, 355.8 |
| MS | CI$^+$ (NH$_3$): 174 | EI: 203<br>CI$^-$ (NH$_3$): 202 | / |
| Melting point by DSC (°C.) | 204 | 188 | 193 (decomposition) |

Furthermore, the structure of the products obtained in the examples was confirmed:
- 1 and 2: 5-amino-3,4-dinitropyrazole
- 3, 4, and 5: 3,4,5-trinitropyrazole
- 6: 4-hydroxy-3,5-dinitropyrazole by X-ray diffraction.

The results obtained are shown, respectively, in attached FIGS. 1, 2, and 3.

With reference to FIG. 2, it is possible to specify that the smallest crystal lattice contains two molecules. The occupation factor of the proton is 0.5 on each nitrogen atom present in the pyrazole ring.

With reference to FIG. 3, it is possible to specify that the molecule crystallizes in the presence of ⅔ of a molecule of water.

Example 7

With argon blanketing at 10° C., 17 mg of sodium hydride are introduced into an anhydrous acetonitrile solution (10 mL) containing 130 mg of 3,4,5-trinitropyrazole. The evolution of hydrogen is immediate and substantial. The reaction mixture is stirred while being left to return to ambient temperature. 400 µL of methyl iodide are then added rapidly, and then the mixture is heated at reflux for 2 hours. The mixture becomes brown over time as a result of the formation of iodine. It is then left to cool, before the mixture is flooded in 50 mL of distilled water. The product is extracted three times with chloroform. The organic phases are combined, dried over magnesium sulfate and evaporated to give 105 mg of yellow liquid. The product (N-methyl-3,4,5-trinitropyrazole) is purified on silica gel. 91 mg (66% yield) of very pale yellow solid are collected in this way. $^1$H NMR (CDCl$_3$) (ppm): 4.42 (s). $^{13}$C NMR (CDCl$_3$) (ppm): 43.2 (CH$_3$), 123.5 (t), 137.7 (t), 148.8 (m). $^{14}$N NMR (CDCl$_3$) (ppm): 343.9, 345.3, 348.0. DSC: melting point: 91.3° C.; evaporation temperature: 243° C.

Example 8

24 mg of sodium hydride (0.98 mmol) are added to a cold solution (0° C.) of 3,4,5-trinitropyrazole in dilution in 10 mL of anhydrous acetonitrile. After a few minutes, Pic-O—

$NH_2$ is added, and then the mixture is left to return to ambient temperature. The mixture is stirred for 3 days. The sodium picrate (yellow solid) which precipitates from the mixture is isolated by filtration. The filtrate is subsequently evaporated to dryness. The product is then purified on silica gel with a heptane/AcOEt mixture (3/1, v/v). The fractions containing the product are combined and then concentrated under vacuum at 20° C. until the product precipitates. 55 mg of white solid (N-amino-3,4,5-trinitropyrazole) are collected in this way. DSC: melting point: 130.5° C.; decomposition temperature: 239° C. $^1H$ NMR ($CD_3NO_2$) (ppm): 7.07 ((broad) s). $^{13}C$ NMR ($CD_3NO_2$) (ppm): 123.1 (t, $J_{CN}$=17 Hz, C(4)-$NO_2$), 136.5 (t, $J_{CN}$=17 Hz, C—$NO_2$), 140.8 (broad, C—$NO_2$). INEPT $^{15}N$ NMR ($CD_3NO_2$) (ppm): −288.7 ($NH_2$, $J_{NH}$=74 Hz). $^{14}N$ NMR ($CD_3NO_2$) (ppm): −31.7, −33.3 (fine), −36.7 (fine). $^1H$ NMR ($CD_3CN$) (ppm): 6.92 ((broad) s). $^{14}N$ NMR ($CD_3CN$) (ppm): −28.3, −29.8 (fine), −33.4 (fine), −68.2. MS (EI): 218.

Attention was focused on the properties and performance characteristics of the products (compounds) of the invention prepared in Examples 1 to 6 above.

a) Sensitivity and Thermal Stability

The sensitivity of the products of the invention and, for comparison, that of ONTA, of HMX and of HNIW (ONTA=5-nitro-1,2,4-triazole-3-one, HMX=octogen, HNIW=CL20=hexanitro-hexaazaisowurtzitane) were assessed with regard to external attacks of mechanical and electrostatic type by means of impact tests, friction tests, and electric spark tests.

The tests carried out are presented below.

Impact sensitivity: The test carried out corresponds to that described in standard NF T 70-500, which is itself similar to the UNO test 3a)ii) from the "Recommendations on the Transport of Dangerous Goods—Manual of Tests and Criteria", fourth revised edition, ST/SG/AC.10/11/Rev.4, ISBN 92-1-239083-81SSN [French version] 1014-7179. By a minimum series of 30 tests, a determination is made of the energy giving rise to 50% (Bruceton method of result analysis) of positive results of an explosive material subjected to the impacts of a drop hammer. The substance under test is confined in a steel device composed of 2 rollers and a guide ring. By modifying the mass and the height of drop of the hammer, the energy can be varied from 1 to 50 J. In view of the small quantity of material available for some of the products tested, a reduced number of reproducibility tests was carried out for said products, relative to the recommendations of the NF T 70-500 standard.

Friction sensitivity: The test carried out corresponds to that described in the standard NF T 70-503, which is itself similar to the UNO test 3b)ii). By a minimum series of 30 tests, a determination is made, using the Bruceton method, of the force which gives rise to 50% of positive results of an explosive material subjected to friction. The substance under test is placed on a porcelain plate of defined roughness, which is moved in a single back-and-forth movement with an amplitude of 10 mm and a speed of 7 cm/s in the empty state, relative to a porcelain peg which rests on the substance. The force applied to the porcelain peg which is drawn over the substance can vary from 7.8 to 353 N. In view of the small quantity of material available for some of the products tested, a reduced number of reproducibility tests was carried out for said products, relative to the recommendations of the NF T 70-500 standard.

Sensitivity to ignition by electric spark: The test carried out is a test developed by the Applicant, with no NF or UNO equivalent. The substance under test, disposed in a boat with a diameter of 10 mm and a height of 1.5 mm, is placed between 2 electrodes and is subjected to an electric spark with a variable energy of 5 to 726 mJ. The system is observed to determine whether there is a pyrotechnic event or not, and a determination is made of the energy threshold at which initiation of the substance is no longer assured. This value is confirmed by 20 tests in succession. In view of the small quantity of material available for some of the products tested, a reduced number of reproducibility tests was carried out for said products.

The thermal stability in turn was determined as follows.

Thermal stability: The thermal stability is analyzed by the method of differential thermal analysis (DSC). Differential thermal analysis consists, within a given temperature range, in characterizing a product by studying the thermicity of the transformations and reactions which it undergoes when subjected to an increase in temperature. The transition temperatures are detected by modifying the heat flow used to heat the sample. The method allows a distinction to be made between the fusion temperatures (m.p.: melting point), boiling temperatures (b.p.: boiling point), and decomposition temperatures (dec.: decomposition).

The results obtained are reported in Table 2 below.

TABLE 2

| Compound | Sensitivity | | | Thermal stability |
|---|---|---|---|---|
| | impact | friction | static electricity | |
| ONTA | 22 J | >353 N | >784 mJ | 286° C. (dec.) |
| HMX | 4 J | 125 N | >726 mJ | 287° C. (dec.) |
| HNIW | 2 J | 80 N | 56-400 mJ | 245° C. (dec.) |
| Exs. 1 and 2 | >50.1 J | >353 N | >784 mJ | 204° C. (m.p.) 214° C. (dec.) |
| Exs. 3, 4, 5 | 17 J | 92 N | >784 mJ | 188° C. (m.p.) 258° C. (b.p.) |
| Ex. 6 | 4.9 J | 183 N | >784 mJ | 193° C. (dec.) | m.p. = melting point
b.p. = boiling point
dec. = decomposition temperature

Appreciation of the values indicated in said Table 2 gives rise to the following comments.

The compounds of the invention post relatively low sensitivities in the various tests. From a general standpoint, the compounds of the present invention are significantly less sensitive than the conventional explosive compounds of nitramine type such as HMX (or octogen). The sensitivities observed for said pyrazoles are similar to that of ONTA or even, in certain cases, are lower than that of ONTA (an outstandingly insensitive explosive). Individually it may be noted that 5-amino-3,4-dinitropyrazole is particularly insensitive to the 3 tests (impact, friction, static electricity). This compound therefore proves to be less sensitive than ONTA. The impact sensitivity of 3,4,5-trinitropyrazole is close to that of ONTA, which is exceptional for a compound possessing such an energy level. This low impact sensitivity is accompanied by a highly appropriate friction sensitivity. 4-Hydroxy-3,5-dinitropyrazole, for its part, is clearly less sensitive to friction and slightly less sensitive than HMX to impact. These safety data clearly make it possible to consider the use of these compounds in energetic materials of reduced vulnerability.

The thermal stabilities are high and are appropriate for applications in explosives and propellants.

b) Performance Characteristics:

The energy level of the products of the invention was determined by means of experimental measurement (X-ray analyses) of their density and by means of calculation of their enthalpy of formation.

The performance characteristics were then calculated in explosion and then in propulsion, for propellant applications, in the presence of binders plasticized with nitro oils. The constituent polymers of said binders are of energetic type (polyglycidyl azide: PGA) or inert polyether type (HTPE: hydroxytelechelic polyether).

The performance results in explosion and in propulsion (calculated for simple compositions without addition of ammonium perchlorate and aluminum) are collated in Table 3 below.

TABLE 3

| Compounds | Enthalpy of formation (kcal/mol) | Exp. density | Detonation rate (m/s) $E/E_{HMX}$ (V/Vo = 2)* | Specific impulse Simple composition (15% HTPE) (s) | Specific impulse Simple composition (30% PGA) (s) |
|---|---|---|---|---|---|
| HMX | 20.1 | 1.908 | 9321 100% | 249.9 | 253.8 |
| RDX | 16.7 | 1.823 | 9008 92% | 250.6 | 254.3 |
| ONTA | −25.7 | 1.910 | 8544 72% | / | / |
| Exs. 1 and 2 | 14.4 | 1.872 | 8640 82% | 220.4 | 230.1 |
| Exs. 3, 4, and 5 | 34.1 | 1.867 | 9253 96% | 261.3 | 261.9 |
| Ex. 6 | −3.6 | 1.92** | 8901 90% | 234.8 | 241.9 |

*Detonation energy liberated, kinetic and internal, for a degree of expansion of the products to twice their initial volume. Reference HMX = 100%.
**The density of the crystal of the hydrated compound (⅔ of water) measured by X-ray is 1.807. The value given in the table is the value calculated for an unhydrated compound.

The results of performance in explosion show that:
3,4,5-trinitropyrazole constitutes a powerful explosive with performance equal to that of octogen (HMX) for a lower impact sensitivity;
5-amino-3,4-dinitropyrazole, a compound insensitive in all of the tests, with a sensitivity lower than that of ONTA (more particularly to impact), constitutes an explosive which features 10% extra energy relative to ONTA.

The results of performance in propulsion show:
in the case of 3,4,5-trinitropyrazole, for applications in simple propellants, a very important gain in terms of specific impulse values, relative to the values obtained with known nitramines such as RDX and HMX (difference greater than 10 s!). This compound even exceeds the performance levels of CL20 (the most highly performing energetic molecule in development known to date). The specific impulse values of CL20 for simple propellants containing 15% of HTPE binder or 30% of PGA binder are 260.1 or 261.5 s respectively. Those of 3,4,5-trinitropyrazole are 261.3 or 261.9 s respectively.

The invention claimed is:
1. 5-Azido-3,4-dinitropyrazole.
2. A process for preparing 5-azido-3,4-dinitropyrazole, comprising reacting 1,3,4-trinitropyrazole with an azide salt.
3. The process according to claim 1, wherein the 1,3,4-trinitropyrazole is obtained by nitration of 3(5)-4-dinitropyrazole.
4. The process according to claim 3, wherein said nitration is carried out in an acetonitric mixture or in a trifluoroacetonitric mixture.
5. The process according to claim 3, wherein said nitration is carried out in a nitronium solution.

* * * * *